(12) United States Patent
Burrell et al.

(10) Patent No.: US 7,353,139 B1
(45) Date of Patent: *Apr. 1, 2008

(54) PORTABLE APPARATUS WITH PERFORMANCE MONITORING AND AUDIO ENTERTAINMENT FEATURES

(75) Inventors: Jonathan C. Burrell, Olathe, KS (US); John H. Lovitt, Spring Hill, KS (US); John C. Conrad, Lee's Summit, MO (US)

(73) Assignee: Garmin Ltd. (KY)

( * ) Notice: Subject to any disclaimer, the term of this patent is extended or adjusted under 35 U.S.C. 154(b) by 527 days.

This patent is subject to a terminal disclaimer.

(21) Appl. No.: 11/059,830

(22) Filed: Feb. 17, 2005

Related U.S. Application Data

(63) Continuation of application No. 10/957,784, filed on Oct. 4, 2004, now Pat. No. 7,085,678, which is a continuation of application No. 10/319,208, filed on Dec. 13, 2002, now Pat. No. 6,853,955.

(51) Int. Cl.
*G06F 11/30* (2006.01)
*G06F 15/00* (2006.01)

(52) U.S. Cl. .................... 702/182; 702/150; 702/188; 701/200; 701/213

(58) Field of Classification Search ................ 702/79, 702/94, 154, 176, 177, 182, 187, 188, 150; 342/357.12, 357.14, 357.15; 701/200, 213
See application file for complete search history.

(56) References Cited

U.S. PATENT DOCUMENTS

| | | | | |
|---|---|---|---|---|
| 5,552,989 A | 9/1996 | Bertrand | ................... | 701/200 |
| 5,583,776 A | 12/1996 | Levi et al. | ................... | 701/217 |
| 6,002,982 A | 12/1999 | Fry | ................... | 701/213 |
| 6,009,138 A * | 12/1999 | Slusky | ................... | 377/5 |
| 6,013,007 A | 1/2000 | Root et al. | ................... | 482/8 |
| 6,024,655 A | 2/2000 | Coffee | ................... | 473/407 |
| 6,032,108 A | 2/2000 | Seiple et al. | ................... | 702/97 |
| 6,067,046 A | 5/2000 | Nichols | ................... | 342/357.14 |
| 6,122,960 A | 9/2000 | Hutchings et al. | ................... | 73/493 |
| 6,132,391 A | 10/2000 | Onari et al. | ................... | 600/595 |
| 6,148,262 A | 11/2000 | Fry | ................... | 701/213 |
| 6,182,010 B1 | 1/2001 | Berstis | ................... | 701/211 |

(Continued)

OTHER PUBLICATIONS

Trimble News Release, dated Jul. 26, 1996 entitled *Trimble Takes to the Road with Race Across America*, 1 page.

(Continued)

*Primary Examiner*—Bryan Bui
(74) *Attorney, Agent, or Firm*—Kevin E. West; Samuel M. Korte

(57) ABSTRACT

A portable apparatus (10) providing both substantially automated performance monitoring and audio entertainment features. In a preferred embodiment the apparatus (10) broadly comprises a portable housing (12); an attachment mechanism (14); a GPS component (16); a heart rate monitor component (17); an audio component (18); a user interface (20); a processor (26); and a power supply (30). The housing (12) may include a headset (1112a) wherein the GPS component (16) is located, and a second housing component (1112b) wherein the processor (26) is located, wherein the GPS component (16) communicates with the processor (26) in a wireless manner. The apparatus (10) is adapted to determine a number of laps or a distance, to provide an elapsed time, and to determine a speed.

5 Claims, 4 Drawing Sheets

U.S. PATENT DOCUMENTS

| | | |
|---|---|---|
| 6,305,221 B1 | 10/2001 | Hutchings ................. 73/488 |
| 6,446,005 B1 | 9/2002 | Bingeman et al. .......... 701/215 |
| 6,463,385 B1 | 10/2002 | Fry ........................ 701/213 |
| 6,498,994 B2 | 12/2002 | Vock et al. ................ 702/44 |
| 6,546,336 B1 | 4/2003 | Matsuoka et al. .......... 701/213 |
| 6,549,845 B2 | 4/2003 | Eackle, Jr. et al. ......... 701/207 |
| 6,549,915 B2 | 4/2003 | Abbott, III et al. ...... 707/104.1 |
| 6,570,532 B2 | 5/2003 | Mise et al. .............. 342/357.1 |
| 6,571,200 B1 | 5/2003 | Mault ....................... 702/182 |
| 6,582,342 B2 | 6/2003 | Kaufman .................... 482/8 |
| 6,594,617 B2 | 7/2003 | Scherzinger ............... 702/160 |
| 6,882,308 B2 * | 4/2005 | Farine et al. ........... 342/357.12 |

OTHER PUBLICATIONS

News from http://lpc1.clpccd.cc.ca.us/lpc/express/Newshome/11-14/GradSpkr.htm entitled *Commencement speaker shares unique vision*, 3 pages.

The Official Publication of the Hang Gliding and Paragliding Association of Canada, vol. 10, Issue 6, Dec. 1996, p. 29.

Garmin GPS 45 and GPS 40 Frequently Asked Question, Oct. 10, 1995, 6 pages.

TRAX publication from http://caribou.c.trincoll.edu/~lkleinbe/trax/manual.txt, taken from web site Sep. 12, 2001, 3 pages.

\* cited by examiner

PORTABLE APPARATUS WITH PERFORMANCE MONITORING AND AUDIO ENTERTAINMENT FEATURES

CROSS REFERENCE TO RELATED APPLICATIONS

This application is a continuation of and claims priority benefit of U.S. patent application Ser. No. 10/957,784, filed Oct. 4, 2004 now U.S. Pat. No. 7,085,678, entitled "PORTABLE APPARATUS WITH PERFORMANCE MONITORING AND AUDIO ENTERTAINMENT FEATURES", which is a continuation of and claims priority benefit of U.S. patent application Ser. No. 10/319,208, filed Dec. 13, 2002, entitled "PORTABLE APPARATUS WITH PERFORMANCE MONITORING AND AUDIO ENTERTAINMENT FEATURES", now U.S. Pat. No. 6,853,955. The above-identified applications are hereby incorporated by reference.

BACKGROUND OF THE INVENTION

1. Field of the Invention

The present invention relates broadly to exercise or other performance monitoring devices, such as, for example, lap or distance counters, or heart rate monitors, and to portable audio entertainment devices, such as, for example, portable cassette tape or compact disk player units. More particularly, the present invention involves a portable apparatus having performance monitoring features facilitated by a global positioning system (GPS) component and a heart rate monitor and audio entertainment features provided by an MP3 player component, wherein the GPS component facilitates substantially automatically determining a number of laps completed or a distance traveled and a speed in doing so, the heart rate monitor provides heart rate information, and the MP3 player component provides selectable, digitally recorded audio entertainment.

2. Description of the Prior Art

It is often desirable when exercising, particularly, for example, when walking, running, or hiking, to monitor a number of laps completed or a distance traveled and a speed in doing so. With regard to counting laps, traditionally an exerciser would attempt to mentally count and remember, without benefit of mechanical or electronic aid, the number of laps completed. Unfortunately, it will be appreciated that the exerciser can often be distracted or otherwise forget the number of laps completed, particularly when a large number of laps are involved. Thus, it is also known to use a mechanical or electronic counting aid wherein the exerciser presses a button or otherwise manually causes a lap counter feature to be incremented upon completion of each lap. Unfortunately, it will be appreciated that the user can often become distracted or otherwise forget to increment the lap counter. Furthermore, it can be cumbersome and inconvenient to have to manually increment the lap counter.

With regard to monitoring speed, traditionally the exerciser would carry a stopwatch or similar timing device and manually stop and start the stopwatch at the end of each lap. Unfortunately, it will be appreciated that carrying two separate devices, including the mechanical or electronic lap counting aid and the stopwatch, can be cumbersome or otherwise undesirable. Furthermore, having to control both devices at the same time can be frustrating. Additionally, the stopwatch provides no mechanism for storing more than one time for later review.

It is also often desirable when exercising to monitor one's heart rate as, for example, an indication of the exercise's physical affect on the exerciser. Heart rate monitors in the form of discrete devices are known in the prior art.

It is also often desirable when exercising to enjoy audio entertainment. It is common, for example, for the exerciser to carry a portable audio entertainment unit, such as, for example, an AM/FM radio, cassette player unit, or compact disk player unit, and to listen to such with the aid of a headset while exercising.

Unfortunately, it will be appreciated that carrying four separate and independent devices, including the mechanical or electronic lap counting aid, the stopwatch, the heart rate monitor, and the audio unit, can be cumbersome and otherwise undesirable. Furthermore, having to both manually increment the lap counter, stop and start the stopwatch, remember to check the heart rate monitor, and operate the audio unit's controls can be frustrating, particularly when the lap counter needs to be incremented or the stopwatch needs to be stopped or started while the exerciser is operating the audio unit's controls. It is these sorts of distraction that can result in the lap counter not being incremented.

Due to the above-identified and other problems and disadvantages in the art, a need exists for an improved mechanism for providing both performance monitoring features and audio entertainment features.

SUMMARY OF THE INVENTION

The present invention overcomes the above-described and other problems and disadvantages in the prior art with a portable apparatus providing both substantially automated performance monitoring and audio entertainment features. The apparatus may be used, for example, by an exerciser or other user on a well-defined closed course (e.g., a track) or on an undefined closed course or on an open course. In a preferred embodiment the apparatus broadly comprises a portable housing; an attachment mechanism; a GPS component; a heart rate monitor component; an audio component; a user interface, including an input portion and an output portion; a processor, including a clock and a memory element; and a power supply.

The portable housing is adapted to contain the remaining components so as to protect and shield them from the hazards of use and of the environment. Thus, for example, the housing is preferably substantially waterproof or resistant. The housing may take any suitable shape, including, for example, ergonomic shapes molded to substantially correspond to a portion of the user's body whereupon or against the housing is meant to rest.

The attachment mechanism is adapted to secure, retain, and maintain the housing in close physical association with the user. As such, the attachment mechanism may take the form of any mechanism suitable to such functionality. The attachment may also provide for adjustment and for elastically accommodating the user's movement and flexibility.

The GPS component is adapted to provide, in a conventional manner, geographic location information based on signals received from two or more members of an array of orbiting satellites. The heart rate monitor component is adapted to determine and communicate the user's heart rate as an indication of the exercise's effect on the user's heart. The heart rate monitor component is substantially conventional in its functioning, and includes a sensor that may be either fixedly integrated into the portable housing or connected to the portable housing and the processor or the user interface by an appropriate electrical connection. The audio component is adapted to both convey monitored or calculated performance information and to provide entertaining talk or music programming. The audio component may include an MP3 player unit for playing digital, pre-recorded programming, and/or an AM/FM radio for playing live broadcasts.

The user interface is adapted both to allow the user to provide input to the processor via the interface's input portion (e.g., one or more buttons or membraneous keypads) and to allow the processor to communicate with the user via the interface's output portion (e.g., a visual display).

The processor is adapted to receive and process information from the GPS component and from the input portion of the interface and to provide information via the audio component and via the output portion of the interface. The clock is used for monitoring elapsed time and for calculating speed. The memory element is used to store information, including, for example, starting location, desired distance, number of laps completed, geographic location, total time, total distance, and average speed. Processing of the information provided by the GPS component and the input portion of the interface involves, at least in part, evaluating a condition. The condition can take at least two distinct forms, including a first condition of returning to a starting location (i.e., completing a lap) or a second condition of traveling a specified distance from the starting location. The processor can also calculate speed, and can evaluate whether the user is traveling slower or faster than a pre-entered target speed.

The power supply, being a rechargeable or non-rechargeable battery, provides power to the various other components of the apparatus.

Thus, it will be appreciated that the apparatus of the present invention provides a number of substantial advantages over the prior art, including, for example, providing performance monitoring features and audio entertainment features in a single apparatus. Thus, users need no longer carry two or three or more separate devices to enjoy the same functionality. Furthermore, the apparatus advantageously provides substantially automated features for counting laps, keeping time, measuring distance, and calculating speed. Thus, the user is no longer burdened with having to remember to increment a lap counter, manually start, stop, and restart a stopwatch, or calculate distances or speeds.

These and other important features of the present invention are more fully described in the section titled DETAILED DESCRIPTION OF A PREFERRED EMBODIMENT, below.

BRIEF DESCRIPTION OF THE DRAWINGS

A preferred embodiment of the present invention is described in detail below with reference to the attached drawing figures, wherein.

DETAILED DESCRIPTION OF A PREFERRED EMBODIMENT

Figure 1:
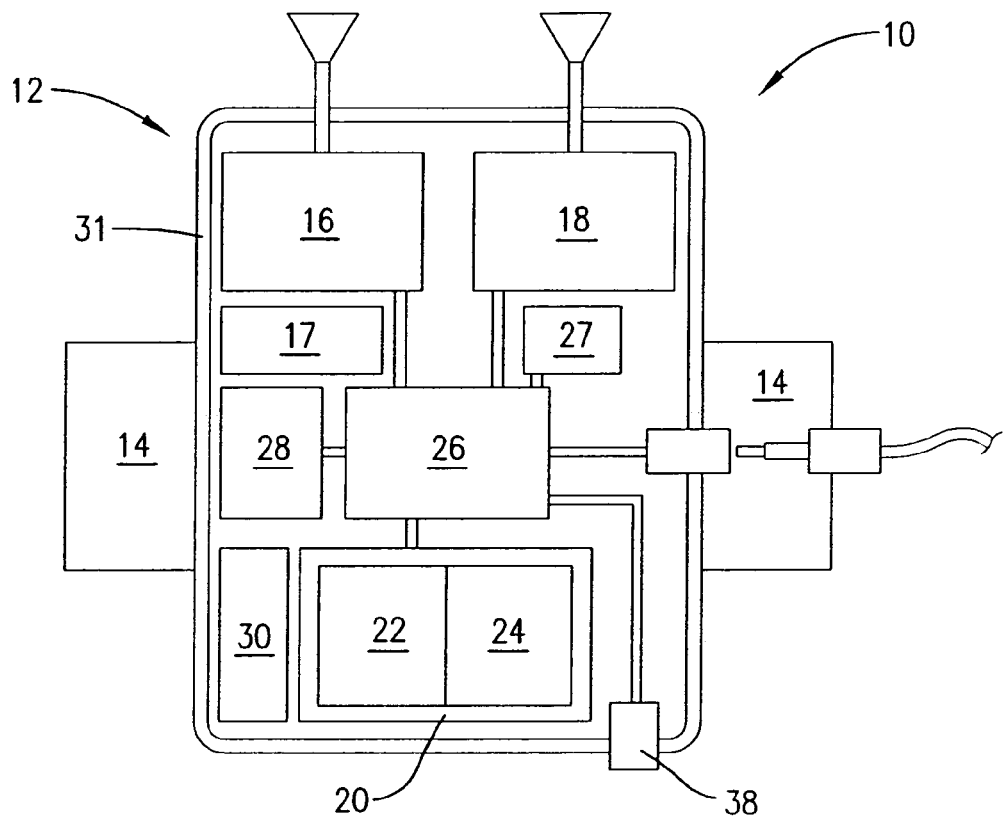
FIG. 1 is a diagram of components in a preferred first embodiment of the apparatus of the present invention.

Referring to FIG. 1, a portable apparatus 10 is shown constructed in accordance with a preferred first embodiment of the present invention. The portable apparatus 10 is adapted to provide both substantially automated performance monitoring and audio entertainment features. The portable apparatus 10 may be used, for example, by an exerciser or other user on a well-defined closed course (e.g., a track) or on an undefined closed course or on an open course.

In the illustrated preferred embodiment, the apparatus 10 broadly comprises a portable housing 12; an attachment mechanism 14; a GPS component 16; a heart rate monitor component 17; an audio component 18; a user interface 20, including an input portion 22 and an output portion 24; a processor 26, including a clock 27 and a memory element 28; and a power supply 30.

The portable housing 12 is adapted to contain the remaining components so as to protect and shield them from the hazards of use (e.g., jostling, dropping, other mechanical shock) and of the environment (e.g., rain, dust). As such, the housing 12 is preferably constructed from a suitable lightweight and impact resistant material such as, for example, plastic, nylon, aluminum, or any combination thereof. Additionally, the housing 12 preferably includes one or more appropriate gaskets or seals to make it substantially waterproof or resistant. Though shown as being substantially rectangular, the housing 12 may take any suitable shape, including, for example, ergonomic shapes molded to substantially correspond to a portion of the user's body (e.g., arm, leg, hip) whereupon or against the housing 12 is meant to rest.

The attachment mechanism 14 is adapted to secure, retain, and maintain the housing 12 in close physical association with the user. As such, the attachment mechanism 14 may take the form of any mechanism suitable to such functionality, including, for example, an armband-type mechanism for securing the housing 12 to the users arm; a waist band-type mechanism for securing the housing 12 to the user's waist; a belt hook-type mechanism for securing the housing 12 to the user's belt or waistband; or an over-the-shoulder-type mechanism for wearing the housing 12 over the user's shoulder. Furthermore, the attachment mechanism is preferably adjustable, using, for example, a conventional buckle or hook-and-loop type mechanism. Additionally, the attachment mechanism is, when appropriate, preferably elastic or otherwise accommodating of the user's movement and flexibility.

The GPS component 16 is adapted to provide, in a conventional manner, geographic location information based on signals received from two or more members of an array of orbiting satellites. This location information is provided to the processor 26.

The heart rate monitor component 17 is adapted to determine and communicate the users heart rate as an indication of the exercise's effect on the user's heart. The heart rate monitor component 17 is substantially conventional in its functioning, and may either be fixedly integrated into the housing 12 or connected to the housing 12 by an appropriate flexible or wireless electrical connection. In the former configuration, the heart rate monitor component 17 may present a sensor on a portion of the housing 12 meant to remain in physical contact with the user. In the latter configuration, the heart rate component 17 may provide the sensor separate from the housing 12 and adapted for wear on the user's body, such as, for example, on a finger or a wrist, with a flexible wire detachably connecting the sensor to the housing 12 and the remainder of the heart rate monitor component 17 located therein. Heart rate information may or may not, as desired, be provided to the processor 26 for processing or storage, and may additionally or alternatively be provided directly to the user interface 20 for display.

The audio component 18 is adapted to provide audible information and entertainment so as to both convey monitored or calculated performance information and provide entertaining talk or music programming. With regard to providing information, the audio component 18 gives voice to electronic output signals generated by the processor 26. With regard to providing entertainment, the audio component 18 includes an MP3 player unit for playing selections of digital, pre-recorded programming. The audio component 18 may also include an AM/FM radio for receiving and communicating live broadcasts of talk or music programming.

Figure 2:
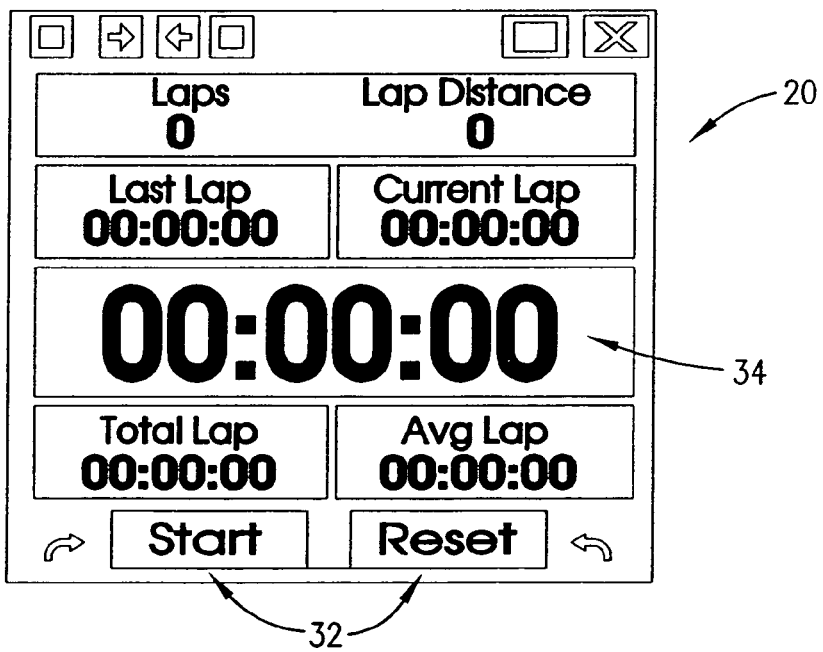
FIG. 2 is a plan view of an interface component of the apparatus of FIG. 1.

Referring also to FIG. 2, the user interface 20 is adapted both to allow the user to provide input to the processor 26 via the input portion 22 of the interface 20 and to allow the processor to communicate with the user via the output portion 24 of the interface 20. The input portion 22 preferably includes one or more buttons, switches, membraneous keypads, or other input mechanisms 32 for providing input to the processor 26. Such input may include, for example, a starting point input indicating the starting location of a lap, or a finish input indicating that the user has completed a series of laps. The output portion 24 preferably includes a visual display 34, such as, for example, an LCD screen, for visually communicating information, such as, for example, the number of laps completed, total time, total distance, speed, and heart rate information.

The processor 26 is adapted to receive and process information from the GPS component 16 and from the input portion 22 of the interface 20 and to provide output information via the audio component 18 and via the output portion 24 of the interface 20. The clock 27 is used for monitoring time, much like a stopwatch, and for calculating speed, as described below. The memory element 28 is used to store or remember information, including, for example, the number of laps completed, geographic locations, total time, total distance, and average speed.

Processing of the information provided by the GPS component 16 and the input portion 22 of the interface 20 involves, at least in part, evaluating a condition. The condition can take at least two distinct forms, including a first condition of returning to a starting location (i.e., completing a lap) or a second condition of traveling a specified distance from the starting location. The user may be given the option of choosing either the first or the second condition as being most appropriate to their particular circumstances.

Figure 3:
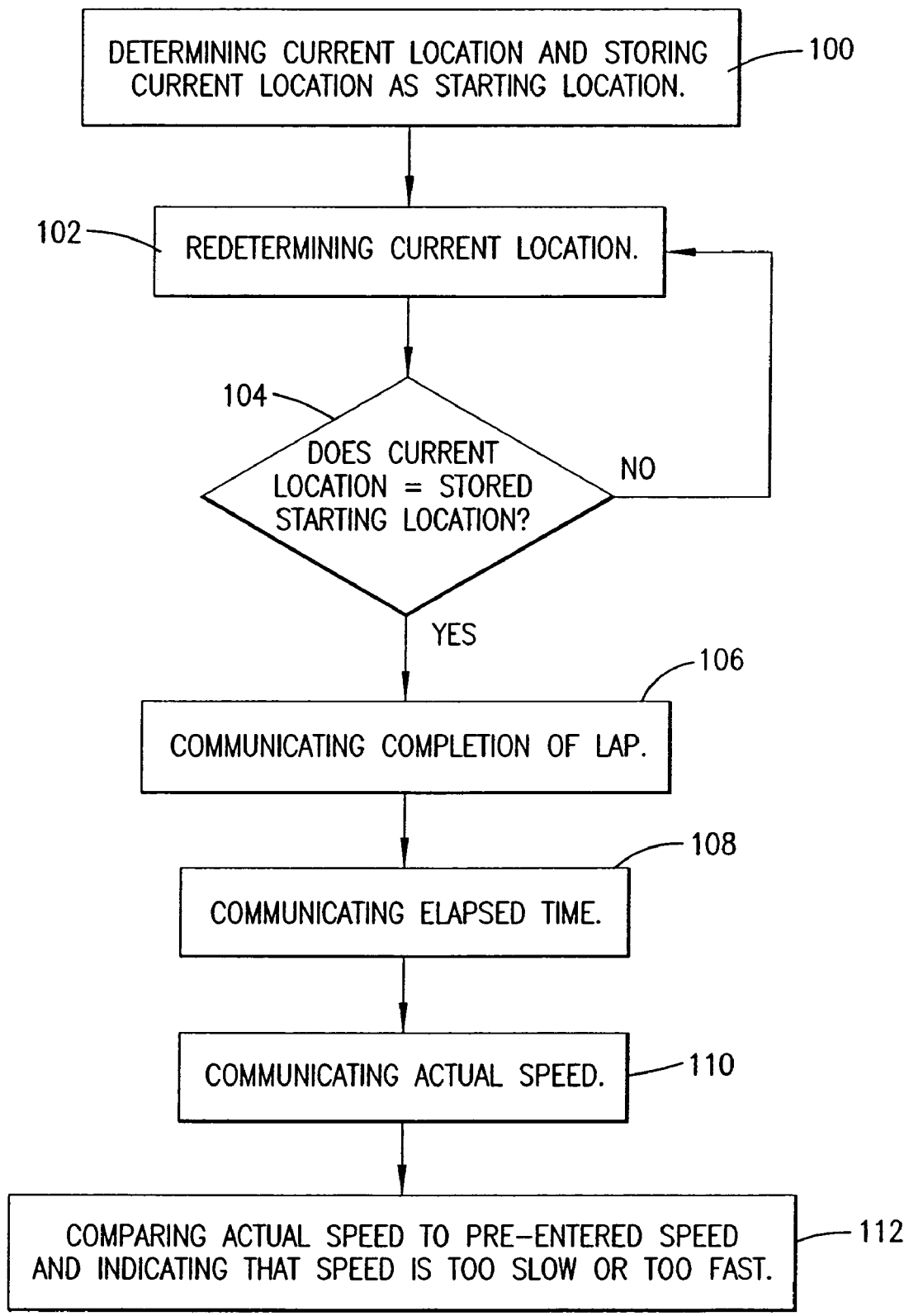
FIG. 3 is a first flowchart of steps involved in the evaluation of a first condition performed by the apparatus of FIG. 1.

Referring also to FIG. 3, the first condition might involve first determining and storing in the memory 28 a starting location, as depicted in box 100. This is initiated when the user presses one of the buttons 32 on the input portion 22 of the interface 20 or otherwise indicates to the processor 26 that the current location is the starting location. Thereafter, the current location is redetermined at periodic intervals, such as, for example, approximately between one second to ten seconds, as depicted in box 102. The condition is evaluated by comparing the starting location with the current location, as depicted in box 104, and, when the two locations substantially match, communicating an output indicating the completion of a lap, as depicted in box 106. As mentioned, the output can be communicated audibly through the audio component 18 as, for example, a short tone, or the output can be communicated via the visual display 34 of the output portion 24 of the interface 20. Furthermore, the elapsed time is stored in the memory 28 and displayed on the visual display 34 of the output portion 24 of the interface 20, as depicted in box 108. Additionally, the processor 26, being able to calculate distance as a function of the difference between one geographic location and another, and being provided with the clock 27 or another suitable timing mechanism, can calculate and communicate speed information, including, for example, average speed over a given distance (e.g., one lap), as depicted in box 110. Speed information might also include the user's instantaneous speed, which might be calculated as average speed over a relatively small distance traveled immediately prior to the calculation. Furthermore, the processor 26 can be programmed to provide a first tone or other indication if the user's pace in completing the lap or other distance is slower than a pre-entered target speed and to provide a second tone or other indication if the user's pace in completing the lap or other distance is faster than the pre-entered target speed, as depicted in box 112.

Figure 4:
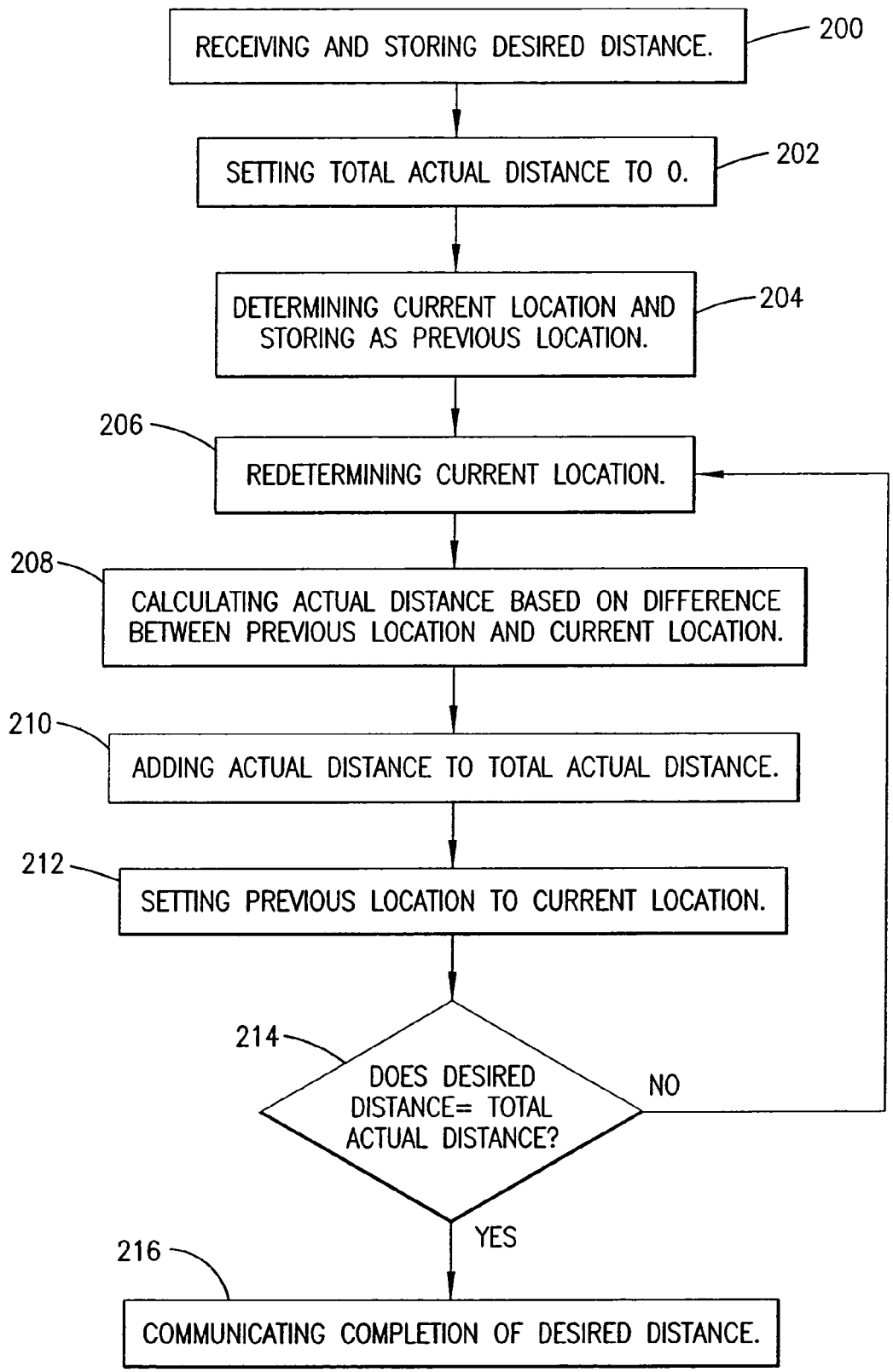
FIG. 4 is a second flowchart of steps involved in the evaluation of a second condition performed by the apparatus of FIG. 1.

Referring also to FIG. 4, the second condition might involve first receiving from the user an input indicating a desired distance and storing this distance in the memory 28, as depicted in box 200. Such an input would be entered using one or more of the buttons 32 on the input portion 22 of the interface 20. Then space is assigned in the memory 28 for storing a total actual distance traveled, and this distance is set to 0, as depicted in box 202. Next, a current or starting location is determined and stored in the memory 28 as a previous location, as depicted in box 204. Then, after an appropriate interval, such as, for example, approximately between one second to ten seconds, the current location is redetermined, as depicted in box 206. Next, the actual distance between the previous location and the current location is calculated and stored in the memory 28, as depicted in box 208. The calculated actual distance is added to the total actual distance stored in the memory 28, as depicted in box 210. Then the previous location is set to the current location, as depicted in box 212. The condition is evaluated by comparing the total actual distance to the inputted desired distance, as depicted in box 214, and, when the two distances substantially match, communicating an audible or visual output indicating such, as depicted inbox 216. If the total actual distance is less than the desired distance, the process repeats from the point of redetermining the current location (box 206).

It will be appreciated that continually comparing the current location with the immediately previous location is more advantageous than continually comparing the current location with the starting location because the route may make substantial twists and turns that may eventually make the distance between the current location and the starting location unrepresentative of the total distance actually traveled. A prime example of this is the case where the user is walking laps around a track such that at periodic intervals the current location and the starting location and the current location are identical, in which case the total distance could mistakenly be calculated as 0.

Use of this second condition may be preferable where there is no clearly defined route to follow or laps to be made, or where the user simply wishes to travel for a predetermined distance before turning around. As described above, elapsed time and average or instantaneous speed can also be provided.

The processor 26 may be provided with a personal computer (PC) connection port 38 to allow the user to transfer information to or from a computing device, including, for example, downloading monitored and stored performance data from the apparatus 10 to a personal computer for later reference or additional processing (e.g., graphing over time).

The power supply 30 provides power to the various other components of the apparatus 10. Preferably the power supply 30 is in the form of a battery, whether rechargeable or non-rechargeable.

In exemplary use and operation, the user, wishing to complete ten laps around a closed course, first presses one of the buttons 32 on the input portion of the interface 20 to indicate that the current location is the starting location from which the completion of each lap is to be determined. The processor 26 receives this starting location and stores it in the memory. The user then controls the MP3 player of the audio component 18 to play a selected digital, pre-recorded song.

Thereafter, as the user travels around the course, every three seconds the processor 26 receives current location information from the GPS component 16. The processor 26 compares the current location with the starting location and, when they substantially match, communicates via the visual display 34 of the output portion 24 of the interface 20 the completion of a lap, the time elapsed in doing so, and the user's average speed. If the user's average speed is slower or faster than a pre-entered minimum or maximum speed, then the processor 26 causes a tone to sound in the user's headset which interrupts or is heard over the playing music. Thus, the laps are counted and the elapsed time is kept substantially automatically, such that the user need only occasionally glance at the visual display 34 to see this information.

Figure 5:
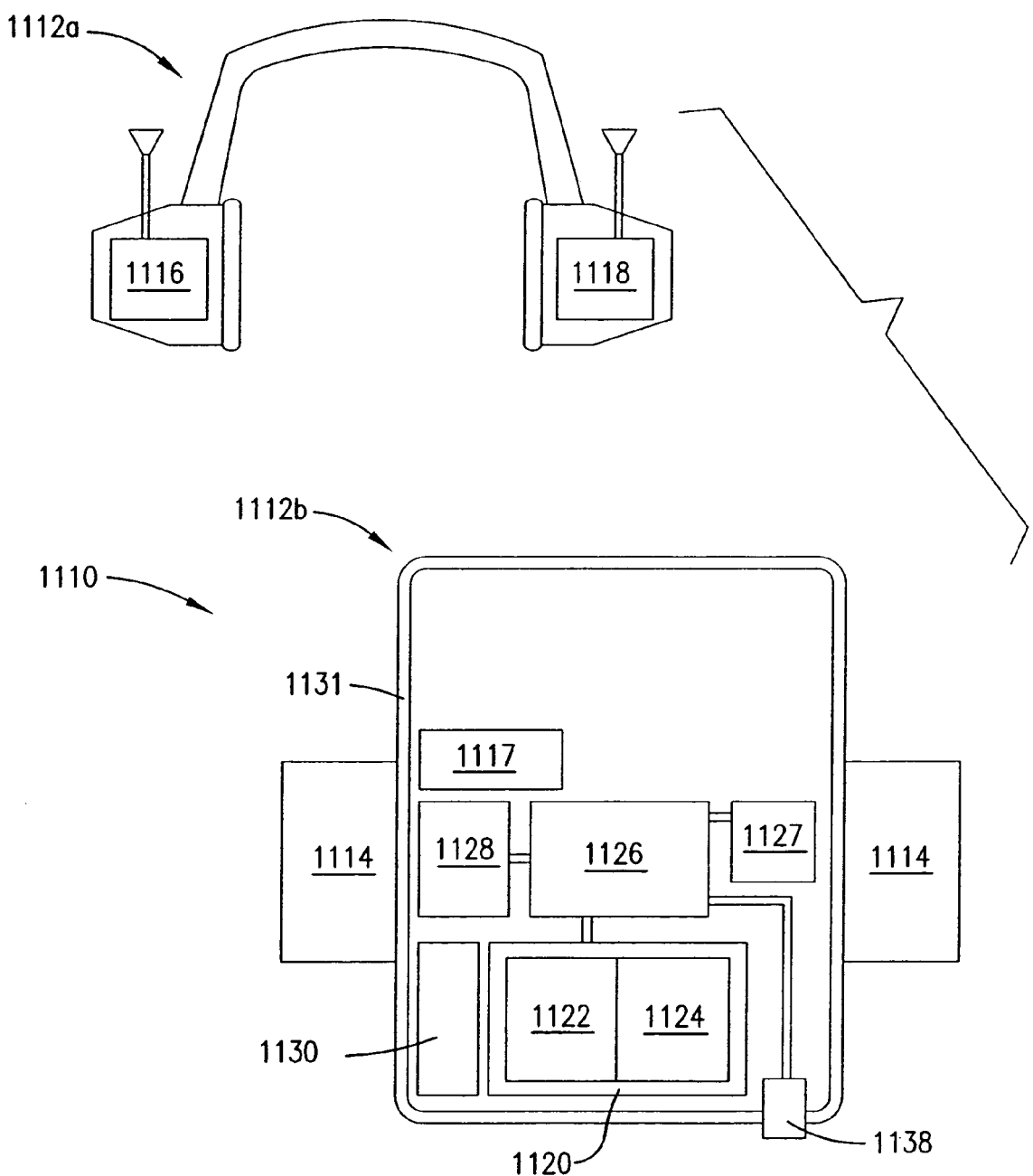
FIG. 5 is a diagram of components in a preferred second embodiment of the apparatus of the present invention.

Referring also to FIG. 5, the portable apparatus 1110 is shown constructed in accordance with a preferred second embodiment which is substantially similar to the above described preferred first embodiment. Thus, the preferred second embodiment includes the GPS component 1116; the heart rate monitor component 1117; the audio component 1118; the user interface 1120, including the input portion 1122 and the output portion 1124; the processor 1126, including the clock 1127 and the memory element 1128; and the power supply 1130.

In the second embodiment, however, there are effectively two housings 1112a,1112b. The first housing 1112a takes the form of a headset to be worn on the user's head, and protectively contains the GPS component 1116 and the audio component 1118. The second housing 1112b is substantially similar in form to the housing of the first embodiment, but contains only the processor 1126, the memory 1128, and the interface 1120. The attachment mechanism 1114 secures the second housing 1112b to the user. Bluetooth-based or similar capabilities allow for wireless communication between the components contained in the first housing 1112a with those contained in the second housing 1112b.

From the preceding description, it will be appreciated that the apparatus of the present invention provides a number of substantial advantages over the prior art, including, for example, providing performance monitoring features and audio entertainment features in a single apparatus. Thus, users need no longer carry two or three or more separate devices to enjoy the same functionality. Furthermore, the apparatus advantageously provides substantially automated features for counting laps, keeping time, measuring distance, and calculating speed. Thus, the user is no longer burdened with having to remember to manually increment a lap counter, start and stop a stopwatch, or determine distances themselves.

Although the invention has been described with reference to the preferred embodiments illustrated in the attached drawings, it is noted that equivalents may be employed and substitutions made herein without departing from the scope of the invention as recited in the claims. It will be appreciated, for example, that the housing and the attachment mechanism may take any practical, functional, ergonomic, or aesthetically desirable shape.

The invention claimed is:

1. A method of monitoring performance, the method comprising the steps of:
   (a) receiving and storing a desired distance;
   (b) determining a starting geographic location and storing the starting geographic location as a previous geographic location;
   (c) setting a total distance to zero;
   (d) determining a current geographic location;
   (e) calculating an actual distance as a difference between the previous geographic location and the current geographic location;
   (f) adding the actual distance to the total distance;
   (g) storing the current geographic location as the previous geographic location; and
   (h) comparing the total distance to the desired distance, and
      if the total distance is substantially identical to the desired distance, communicating completion of the desired distance, and
      if the total distance is less than the desired distance, repeating steps (d) through (h).

2. The method as set forth in claim 1, further including the steps of:
   (i) communicating an elapsed time; and
   (j) calculating an actual speed based on the elapsed time and the total distance.

3. The method as set forth in claim 2, further including the steps of:
   (k) receiving an input indicating a desired target speed; and
   (l) comparing the desired target speed to the actual speed and communicating a difference if the actual speed is different than the desired target speed.

4. The method as set forth in claim 2, further including the step of (m) transferring the actual speed, the elapsed time, and the distance difference to a computing device for storage.

5. The method as set forth in claim 1, further including the step of (n) determining and communicating a heart rate of a user.

* * * * *